United States Patent [19]

Erpenbach et al.

[11] 4,430,273
[45] Feb. 7, 1984

[54] PRODUCTION OF ACETIC ANHYDRIDE

[75] Inventors: Heinz Erpenbach, Cologne; Klaus Gehrmann, Erftstadt; Hans-Klaus Kübbeler, Swisttal; Klaus Schmitt, Erfstadt, all of Fed. Rep. of Germany

[73] Assignee: Hoechst Aktiengesellschaft, Fed. Rep. of Germany

[21] Appl. No.: 366,344

[22] Filed: Apr. 7, 1982

[30] Foreign Application Priority Data

Aug. 17, 1978 [DE] Fed. Rep. of Germany ....... 2836084

[51] Int. Cl.$^3$ .............................................. C07C 51/12
[52] U.S. Cl. .................................... 260/546; 260/549
[58] Field of Search ................................ 260/546, 549

[56] References Cited

U.S. PATENT DOCUMENTS 3,852,346 12/1974 Forster ................................. 260/546
4,115,444 9/1978 Rizkalla ............................... 260/549

OTHER PUBLICATIONS

Klingsburg, Pyridine, pp. 3–5 (1961).
Cram et al., Organic Chemistry, p. 590 (1964).

Primary Examiner—Robert Gersil
Attorney, Agent, or Firm—Connolly and Hutz

[57] ABSTRACT

The invention provides a process for making acetic anhydride, wherein methyl acetate and/or dimethylether is (are) reacted with carbon monoxide under substantially anhydrous conditions, at temperatures of 350 to 575 K and under pressures of 1 to 300 bars in the presence of a catalyst system comprised of noble metals belonging to group VIII of the periodic system of the elements, or their compounds and iodine and/or its compounds. More specifically, an aliphatic carboxylic acid with 1 to 8 carbon atoms and at least one heterocyclic aromatic compound, in which at least one hetero atom is a quaternary nitrogen atom are used as promoters.

7 Claims, No Drawings

PRODUCTION OF ACETIC ANHYDRIDE

This invention relates to a process for making acetic anhydride by reacting methyl acetate and/or dimethylether with carbon monoxide under substantially anhydrous conditions at temperatures of 350 to 575 K., under pressures of 1 to 300 bars and in the presence of a catalyst system comprised of noble metals belonging to group VIII of the periodic system or their compounds and iodine and/or its compounds, which comprises: using, as promoters, an aliphatic carboxylic acid having 1 to 8 carbon atoms and at least one heterocyclic aromatic compound, in which at least one of the hetero atoms is a quaternary nitrogen atom.

A process for making monocarboxylic anhydrides has already been described in U.S. Pat. No. 4,115,444, which is comparable with the present process save that a noble metal belonging to group VIII of the periodic system and an iodide are used therein in combination with a multiple promoter containing metal, preferably chromium, iron, cobalt, nickel and an organonitrogen compound or organophosphorus compound with trivalent nitrogen or phosphorus.

The process disclosed in German Patent Specification "Offenlegungsschrift" No. 26 10 036 is seriously handicapped by the fact that the metal compounds and secondary products of the multiple promoter are substantially insoluble in boiling acetic anhydride, so that the circulation of the catalyst/promoter-system, which is necessary for continuous operation, is rendered very difficult or even impossible. In addition to this, the above insoluble compounds have been found to unduly affect the separation of acetic anhydride from the catalyst/promoter-system. As a result, it is necessary for the expensive noble metal-containing catalyst to be subjected to cumbersome intermediate processing treatment with undesirable loss of valuable catalyst and rapid adverse effects on the activity of the entire system. These are the reasons why the process just described has not been commercialized heretofore.

In accordance with our present invention which avoids the adverse effects described hereinabove, we have unexpectedly found that it is possible for the promoter mixture to be left free from difficultly soluble metal salts, e.g. of chromium, provided that a heterocyclic aromatic compound containing quaternary nitrogen and an aliphatic carboxylic acid with 1 to 8 carbon atoms are substituted for the organonitrogen compound or organophosphorus compound containing trivalent nitrogen or phosphorus. Under the reaction conditions of our present process, the addition compounds with quaternary nitrogen are in the form of a melt and do in no way interfere with the circulation of the catalyst system. Nor do the substitute products of this invention impair the selectivity of the catalyst system of which the activity is even considerably improved. Both under the reaction conditions and the conditions selected for the work up of the products obtained by the carbonylation of methyl acetate or dimethylether, the heterocyclic aromatic compounds with at least one quaternary nitrogen as the hetero atom, which are used in this invention individually or in combination, are in the form of a melt which is a suitable solvent for the noble metal complexes and also readily miscible with acetic anhydride.

Addition products, which have the properties specified above, comprise, for example:

(a) N-methylpyridinium iodide; N,N-dimethylimidazolium iodide; N-methyl-3-picolinium iodide; N-methyl-2,4-lutidinium iodide; N-methyl-3,4-lutidinium iodide; N-methyl-quinolinium iodide;

(b) pyridinium acetate; N-methylimidazolium acetate; 3-picolinium acetate; 2,4-lutidinium acetate; 3,4-lutidinium acetate.

The promoter properties of these addition products are considerably improved in the presence of an aliphatic carboxylic acid with 1 to 8 carbon atoms.

Further preferred features of the present invention provide:

(a) for the heterocyclic compound used to have a melting point or mixed melting point of less than 413 K., which is the boiling point of acetic anhydride;

(b) for the heterocyclic compounds to be used in the form of their addition products with acetic acid or methyl iodide;

(c) for the catalyst/promoter-system comprised of noble metal (compound)/iodine(compound)/carboxylic acid/heterocyclic compound to be used in an atomic or molar ratio of 1:(1–1400):(10–2000):(1–1200); and (d) for the carbon monoxide/hydrogen-mixture to contain up to 10 volume % of hydrogen.

The process of the present invention should preferably be effected at temperatures of 400 to 475 K. and under pressures of 20 to 150 bars. It is also preferable to use 0.0001 to 0.01 mol of the noble metal belonging to group VIII of the periodic system of the elements or its compounds per mol of methyl acetate and/or dimethylether. Further preferred features provide for the catalyst/promoter-system of noble metal (compound)/iodine (compound)/carboxylic acid/heterocyclic compound to be used in an atomic or molar ratio of 1:(10–300):(25–600):(10–300), and for acetic acid to be used as the carboxylic acid.

The invention will now be described with reference to the accompanying diagrammatic representation showing a typical form of flow scheme for carrying out the present process.

Methyl acetate and/or dimethylether and carbon monoxide or a mixture of CO and $H_2$ containing up to 10 volume % of $H_2$ are placed in an autoclave 1 made up of Hastelloy C and reacted therein under a preferred pressure of 20 to 150 bars and at a preferred temperature of 400 to 475 K. to give acetic anhydride, the reaction being effected in the presence of a catalyst system comprised of one or more noble metals belonging to group VIII of the periodic system or their compounds and iodine and/or its compounds, preferably methyl iodide, and in the presence of a carboxylic acid, preferably acetic acid, and at least one heterocyclic aromatic compound, in which at least one hetero atom is a quaternary nitrogen atom as promoters. The bulk of unreacted carbon monoxide and hydrogen, if any, is circulated by means of a gas recirculation pump 2, whilst a fraction thereof is allowed to issue from the system via a scrubbing stage 3. Fresh carbon monoxide, which may be used in admixture with hydrogen, is introduced into the gas under circulation via a conduit 4 in metered proportions corresponding to the conversion rate. Fresh methyl acetate and/or dimethylether are supplied in quantities corresponding to the conversion rate via a conduit 5 opening into the upper portion of the scrubbing stage 3 and introduced into the reactor 1 through a conduit 6. The reaction mixture issues from the reactor 1 through a conduit 7. The distilling column 8 is used to effect the separation of the low-boiling fractions (methyl acetate or dimethylether, methyl iodide) which are recycled to the reactor 1 via conduits 9 and 6. Material accumulating in the base portion of column 8 is delivered to an evaporator 10 and separated into distillate and catalyst. This latter is recycled through conduits 11, 9 and 6 into the reactor 1. The distillate recovered in the evaporator 10 is separated in distilling column 12 into acetic acid, which is recycled to the reactor 1 through conduits 13, 11, 9 and 6, and acetic anhydride, which is removed through conduit 14.

EXAMPLE 1

250 g of methyl acetate, 1.6 g of $RhCl_3.3H_2O$, 50 g of $CH_3I$, 50 g of acetic acid and 60 g of N-methyl-3-picolinium iodide were placed in a Hastelloy autoclave and reacted therein with CO under a pressure of 40 bars and at a temperature of 450 K. The product obtained after a reaction period of 45 minutes was analyzed and 271 g of acetic anhydride, corresponding to 578 g of $Ac_2O$ per g Rh per hour, was found to have been formed.

EXAMPLE 2

250 g of methyl acetate, 1.6 g of $RhCl_3.3H_2O$, 100 g of $CH_3I$, 60 g of acetic acid and 120 g of N-methyl-3-picolinium iodide were placed in a Hastelloy autoclave and reacted therein with CO at 60 bars and 450 K. The product obtained after a reaction period of 32 minutes was analyzed and 276 g of acetic anhydride, corresponding to 828 g of $Ac_2O$ per g Rh per hour, was found to have been formed.

EXAMPLE 3

250 g of methyl acetate, 0.2 g of $RhCl_3.3H_2O$, 140 g of $CH_3I$, 80 g of acetic acid and 180 g of N-methyl-3-picolinium iodide were placed in a Hastelloy autoclave and reacted therein with CO at 50 bars and 450 K. The product obtained after 78 minutes was analyzed and 271 g of acetic anhydride, corresponding to 2667 g of $AcO_2$ per g Rh per hour, was found to have been formed.

EXAMPLE 4

250 g of methyl acetate, 1.6 g of $RhCl_3.3H_2O$, 80 g of $CH_3I$, 50 g of acetic acid and 100 g of N-methyl-quinolinium iodide were placed in a Hastelloy autoclave and reacted therein with CO at 35 bars and 455 K. 278 g of acetic anhydride, corresponding to 919 g of $Ac_2O$ per g Rh per hour, was obtained after a reaction period of 29 minutes.

EXAMPLE 5

250 g of methyl acetate, 1.6 g of $RhCl_3.3H_2O$, 60 g of $CH_3I$, 70 g of acetic acid and 70 g of N,N-dimethylimidazolium iodide were placed in a Hastelloy autoclave and reacted therein with CO at 50 bars and 450 K. The reaction mixture obtained after a reaction period of 31 minutes was found to contain 283 g of acetic anhydride, corresponding to 876 g of $Ac_2O$ per g Rh per hour.

EXAMPLE 6

250 g of methyl acetate, 1.6 g of $RhCl_3.3H_2O$, 80 g of $CH_3I$, 100 g of acetic acid and 180 g of N,N-dimethylimidazolium iodide were placed in a Hastelloy autoclave and reacted therein with CO at 30 bars and 443 K. 273 g of acetic anhydride, corresponding to 1092 g of $Ac_2O$ per g Rh per hour, was found to have been formed after a reaction period of 24 minutes.

EXAMPLE 7

250 g of methyl acetate, 1.5 g of $RhCl_3.3H_2O$, 60 g of $CH_3I$, 60 g of acetic acid and 60 g of N,N-dimethylimidazolium iodide were placed in a Hastelloy autoclave and reacted therein at 450 K. and 50 bars with a mixture of CO and $H_2$, which contained 8 volume % of $H_2$. The reaction mixture obtained after a reaction period of 34 minutes was found to contain 279 g of acetic anhydride, corresponding to 840 g of $Ac_2O$ per gram Rh per hour, and traces of ethylidene diacetate.

EXAMPLE 8

250 g of methyl acetate, 2 g of $Pd(CH_3CO_2)_2$, 40 g of $CH_3I$, 80 g of acetic acid and 50 g of N,N-dimethylimidazolium iodide were placed in a Hastelloy autoclave and reacted therein with CO at 450 K. and 50 bars. The reaction mixture obtained after 132 minutes was analyzed and found to contain 191 g of acetic anhydride, corresponding to 91 g of $Ac_2O$ per g Pd per hour.

EXAMPLE 9

250 g of methyl acetate, 2 g of $RhCl_3.3H_2O$, 15 g of $CH_3I$, 10 g of acetic acid and 30 g of N-methyl-3,4-lutidinium iodide were placed in a Hastelloy autoclave and reacted therein with CO at 150 bars and 455 K. The reaction mixture obtained after a reaction period of 135 minutes was analyzed and 259 g of acetic anhydride, corresponding to 147 g of $Ac_2O$ per gram Rh per hour, was found to have been formed.

EXAMPLE 10

250 g of methyl acetate, 1.8 g of $IrCl_3$, 50 g $CH_3I$, 60 g of acetic acid and 80 g of N-methyl-2,4-lutidinium iodide were placed in a Hastelloy autoclave and reacted therein with CO at 120 bars and 470 K. The reaction mixture obtained after a reaction period of 84 minutes was analyzed and 269 g of acetic anhydride, corresponding to 166 g of $Ac_2O$ per g Ir per hour, was found to have been formed.

EXAMPLE 11

250 g of methyl acetate, 1.6 g of $RhCl_3.3H_2O$, 50 g of $CH_3I$, 50 g of acetic acid, 20 g of N-methylpyridinium iodide and 40 g of N-methyl-3-picolinium iodide were placed in a Hastelloy autoclave and reacted therein with CO at 450 K. and 30 bars. The reaction mixture obtained after a reaction period of 39 minutes was found to contain 276 g of acetic anhydride, corresponding to 679 g of $Ac_2O$ per gram Rh per hour.

EXAMPLE 12

250 g of methyl acetate, 1 g of $RhCl_3.3H_2O$, 50 g of $CH_3I$, 50 g of acetic acid, 15 g of N-methylpyridinium iodide and 30 g of N-methyl-2,4-lutidinium iodide were placed in a Hastelloy autoclave and reacted therein with CO at 430 K. and 50 bars. The reaction mixture obtained after 170 minutes was analyzed and found to contain 269 g of acetic anhydride, corresponding to 243 g of $Ac_2O$ per gram Rh per hour.

EXAMPLE 13

250 g of methyl acetate, 0.8 g of $RhCl_3.3H_2O$, 100 g of $CH_3I$, 90 g of acetic acid, 120 g of N,N-dimethylimidazolium iodide and 60 g of N-methyl-3-picolinium iodide were placed in a Hastelloy autoclave and reacted therein with CO at 100 bars and 445 K. The reaction mixture obtained after a reaction period of 38 minutes was found to contain 278 g of acetic anhydride, corresponding to 1402 g of Ac$_2$O per g Rh per hour.

EXAMPLE 14

250 g of methyl acetate, 1.6 g of RhCl$_3$.3H$_2$O, 60 g of CH$_3$I, 50 g of acetic acid and 40 g of pyridinium acetate were placed in a Hastelloy autoclave and reacted therein with CO at 450 K. and 50 bars. The reaction mixture obtained after a reaction period of 51 minutes was found to contain 273 g of acetic anhydride, corresponding to 514 g of Ac$_2$O per g Rh per hour.

EXAMPLE 15

250 g of methyl acetate, 0.6 g of RhCl$_3$.3H$_2$O, 150 g of CH$_3$I, 75 g of acetic acid and 100 g of N-methylimidazolium acetate were placed in a Hastelloy autoclave and reacted therein with CO at 460 K. and 60 bars. 281 g of acetic anhydride, corresponding to 1012 g of Ac$_2$O per g of Rh per hour, was found to have been formed, after a reaction period of 71 minutes.

EXAMPLE 16

200 g of dimethylether, 1.8 g of RhCl$_3$.3H$_2$O, 70 g of CH$_3$I, 60 g of acetic acid and 90 g of N-methyl-3-picolinium iodide were placed in a Hastelloy autoclave and reacted therein with CO at 440 K. and 80 bars. The methyl acetate-containing reaction mixture obtained after a reaction period of 126 minutes was found to contain 209 g of acetic anhydride, corresponding to 141 g of Ac$_2$O per g Rh per hour.

EXAMPLE 17

A continuously operated test apparatus made up of Hastelloy alloy was used. The reactor which was filled with 2 liters of reaction mixture was supplied with 2.2 kg/h of fresh methyl acetate. The mean reaction temperature was 450 K. and a pressure of 50 bars was established by the continuous introduction of CO. The mixture coming from the reactor contained about 9 weight % of methyl acetate, about 55 weight % of acetic anhydride, about 10 weight % of acetic acid, about 10 weight % of methyl iodide and about 13 weight % of quaternary salt (molar ratio of N-methyl-3-picolinium iodide to N,N-dimethylimidazolium iodide=1:2). The rhodium concentration (RhCl$_3$.3H$_2$O) in the reaction mixture was about 18 millimols of Rh per liter of reaction mixture. The mixture was worked up distillatively and recycled in the manner described herein with reference to the accompanying flow scheme. About 3 kg/h of acetic anhydride was obtained. This corresponded to a space/timeyield of 1500 g of Ac$_2$O per liter per hour or to 811 g of Ac$_2$O per g Rh per hour. The anhydride yield, based on the methyl acetate which underwent conversion, was almost quantitative.

EXAMPLE 18

250 g of methyl acetate, 1.6 g of RhCl$_3$.3H$_2$O, 50 g of methyl iodide, 40 g of formic acid and 60 g of N,N-dimethylimidazolium iodide were placed in a Hastelloy autoclave and reacted therein with CO at 50 bars and 450 K. The reaction mixture obtained after a reaction period of 68 minutes was found to contain 278 g of acetic anhydride, corresponding to 392 g of Ac$_2$O per g Rh per hour.

EXAMPLE 19

250 g of methyl acetate, 1.6 g of RhCl$_3$.3H$_2$O, 50 g of methyl iodide, 60 g of propionic acid and 60 g N,N-dimethylimidazolium iodide were placed in a Hastelloy autoclave and reacted therein with CO at 50 bars and 450 K. The reaction mixture obtained after a reaction period of 52 minutes was analyzed and found to contain 274 g of acetic anhydride, corresponding to 505 g of Ac$_2$O per g Rh per hour.

EXAMPLE 20

250 g of methyl acetate, 1.6 g of RhCl$_3$.3H$_2$O, 50 g of methyl iodide, 75 g of butyric acid and 60 g of N,N-dimethylimidazolium iodide were placed in a Hastelloy autoclave and reacted therein with CO at 60 bars and 450 K. The reaction mixture obtained after a reaction period of 58 minutes was found to contain 270 g of acetic anhydride, corresponding to 446 g of Ac$_2$O per g Rh per hour.

We claim:

1. A process for making acetic anhydride by reacting at least one substance selected from methyl acetate and dimethylether with carbon monoxide under substantially anhydrous conditions, at temperatures of 350 to 575 K. and under pressures of 1 to 300 bars in the presence of a catalyst system comprised of noble metals belonging to group VIII of the periodic system of the elements or their compounds and at least one substance selected from iodine and its compounds, which comprises using a promoter system consisting essentially of an aliphatic carboxylic acid with 1 to 8 carbon atoms and at least one heterocyclic aromatic compound, in which at least one hetero atom is a quaternary nitrogen atom.

2. A process as claimed in claim 1, wherein the heterocyclic compounds used have a melting point or mixed melting point of less than 413 K., which is the boiling point of acetic anhydride.

3. A process as claimed in claim 1, wherein the heterocyclic compounds are used in the form of their addition products with acetic acid or methyl iodide.

4. A process as claimed in claim 1, wherein the catalyst/promoter-system comprised of noble metal (compound) iodine (compound)/carboxylic acid/heterocyclic compound is used in the molar ratio of 1:(1–1400):(-10–2000):(1–1200).

5. A process according to claim 1 which comprises the step of:
introducing into the reaction medium the said catalyst system and a promoter system consisting essentially of an aliphatic carboxylic acid with 1 to 8 carbon atoms and at least one heterocyclic aromatic compound in which at least one hetero atom is a quaternary nitrogen atom, said heterocyclic aromatic compound being in quaternary ammonium salt form prior to its introduction into the reaction medium.

6. A process according to claim 7 wherein, subsequent to said introducing step, the reaction of methyl acetate or dimethylether with carbon monoxide is carried out with continuous introduction of fresh carbon monoxide and fresh methyl acetate or dimethylether.

7. A process according to claim 1 wherein said promoter system is essentially free of non-noble promoter metals and non-noble promoter metal salts.

* * * * *